United States Patent [19]

Hewertson et al.

[11] 4,130,598
[45] Dec. 19, 1978

[54] 2,5-DIMETHYL-2,4-HEXADIENE PRODUCTION

[75] Inventors: Warren Hewertson; David Holland; David J. Milner, all of Runcorn, England

[73] Assignee: Imperial Chemical Industries Limited, London, England

[21] Appl. No.: 702,130

[22] Filed: Jul. 2, 1976

[30] Foreign Application Priority Data

Jul. 2, 1975 [GB] United Kingdom ............... 27923/75

[51] Int. Cl.² ............................................. C07C 11/12
[52] U.S. Cl. ............................. 260/680 R; 260/654 D
[58] Field of Search ........... 260/680 R, 654 R, 654 D

[56] References Cited

U.S. PATENT DOCUMENTS

| 2,818,441 | 12/1957 | Vaughan et al. | 260/680 R |
| 3,406,210 | 10/1968 | Schmerling | 260/648 R |
| 3,472,908 | 10/1969 | Harder | 260/680 R |
| 3,819,731 | 6/1974 | Pitt et al. | 260/654 R |

OTHER PUBLICATIONS

Rust et al., "Decomposition of Di-t-Alkyl Peroxides", J.A.C.S., vol. 70, No. 95, pp. 95-99 (1948).
Henne et al., "Olefins and Diolefins from Allylic Chlorides", J.A.C.S., vol. 63, pp. 3474-3476 (1941).
Petrov et al., "High Temperature Condensation of Tetrachlorethylene with Aromatic Hydrocarbons & Olefins", *Doklady Akademii Nauk SSSR*, vol. 131, No. 5, pp. 1098-1011, Apr. 1960.

*Primary Examiner*—Brian Hearn
*Attorney, Agent, or Firm*—Cushman, Darby & Cushman

[57] ABSTRACT

Process for the production of 2,5-dimethyl-1,5-hexadiene by heating isobutene with a 1,1,2-trihalo ethylene in the vapor phase in the presence of a free-radical generator. The free-radical generator is preferably a peroxide and the reaction temperature in the range 200°–600° C. The product may be readily isomerized to 2,5-dimethyl-2,4-hexadiene, which is useful as an insecticide intermediate.

5 Claims, No Drawings

2,5-DIMETHYL-2,4-HEXADIENE PRODUCTION

This invention relates to the manufacture of 2,5-dimethyl-1,5-hexadiene.

In our copending British patent application No. 27923/75 we describe a process for the manufacture of 1,1-dihalo-4-methylpentadienes by reacting isobutene with a 1,1,2-trihaloethylene in the vapour phase at elevated temperature. However when the reaction is conducted in the presence of a free-radical generator, e.g., a peroxide, 2,5-dimethyl-1,5-hexadiene, a non-halogenated dehydrodimer of isobutene may also be produced in worthwhile yield. This compound may be readily isomerised to 2,5-dimethyl-2,4-hexadiene which is useful as an insecticide precursor.

Previously proposed methods for producing 2,5-dimethyl-hexadiene have involved several stages, including costly and time-consuming operations. Furthermore, previously reported reactions in which olefins are coupled in the presence of peroxides to give dehydrodimers have been in the liquid-phase, giving low yields of our desired product or gas-phase in which there was either no yield of such a product or a moderate yield and then only when the reaction was conducted at very high temperatures.

It is thus surprising that when isobutene is dehydrodimerised in the presence of peroxides and a haloethylene a good yield of 2,5-dimethyl-1,5-hexadiene may be obtained in a single step.

According to the present invention, a process for the production of 2,5-dimethyl-1,5-hexadiene comprises reacting isobutene with a 1,1,2-trihaloethylene at elevated temperature in the vapour phase in the presence of a free-radical generator.

The free-radical generator is preferably a peroxide, especially an organic peroxide, for example t-butylhydroperoxide or di-t-butylperoxide; but other peroxides, for example hydrogen peroxide, may be used. The concentration of free-radical generator may be varied considerably; but will generally be in the range 0.05 to 5.0 mole %, the optimum concentration for particular reaction temperatures and/or other conditions and for the particular free-radical generator used being readily determined by experiment. However, concentrations up to 2 mole % are generally sufficient.

Reaction temperatures in the range 200° C. to 600° C. are generally suitable; but the final choice of temperature range will depend upon the desired product distribution and the nature of the free-radical generator being used. For example, if a high ratio of 2,5-dimethyl-1,5-hexadiene to halogenated dienes is desired, temperatures at the lower end of the range (e.g. 250° to 400° C.) are preferred. However, if the aim is high conversion to dimethylhexadiene based on free-radical generator consumed, temperatures in the range 400° to 550° C. should be used. It will also be appreciated that the temperature used must be sufficiently high to enable free-radicals to be generated. Thus, for example, when hydrogen peroxide is used, temperatures of at least 400° C. should be used. In addition to the above-mentioned considerations, at temperatures above 450° C. the trihaloethylene tends to decompose and generate radicals which themselves may yield our desired dimethyl-hexadiene product, thus enhancing the overall yield of product based on free-radical generator present.

The trihaloethylenes which may be used in this invention are preferably the chloro or bromo derivatives, and may also contain both chlorine and bromine atoms. Examples of suitable trihaloethylenes include 1,1,2-trichloroethylene and 1,1-dichloro-2-bromoethylene.

The ratio of isobutene to trihaloethylene may be varied over wide limits; but generally it will be in the range 10/1 to 1/10. However, if it is desired to coproduce 2,5-dimethyl-1,5-hexadiene and 1,1-dihalo-4-methylpentadienes, ratios in the range 1/3 to 3/1 are preferred.

The residence time in the reaction zone must obviously be sufficient for a substantial fraction of the radical generator to decompose into free radicals; but generally it is in the range 5 to 30 seconds, preferably from 10 to 20 seconds.

The process may conveniently be performed by passing the gaseous mixture, including the free radical generator, through a reactor which may be, for example, a heated glass or metal tube, and cooling the exit gases to separate out the high boiling fraction which normally contains the dimethyl-hexadiene and any chlorinated dienes which which have been coproduced. Since the 2,5-dimethyl-1,5-hexadiene has a boiling point of 114° C., which is close to those for the trihaloethylenes, e.g. 84° C. for trichloroethylene, the dimethyl-hexadiene may co-distill with the trihaloethylene, as this is commonly present in excess. However, we have found that if the 2,5-dimethyl-1,5-hexadiene is first isomerised to the conjugated 2,5-dimethyl-2,4-hexadiene, this isomer, having a higher boiling point, does not co-distill and hence separation is much easier. The isomerisation is readily achieved by heating with a suitable conversion catalyst (e.g. p-toluene sulphonic acid) preferably at a temperature in the range 100° to 170° C. A convenient procedure comprises removing the isobutene and most of the trihaloethylene by gentle heating at a temperature ≯ the boiling point of the trihaloethylene and then heating the residual reaction mixture, preferably under elevated pressure (e.g. up to 2 ats) at a temperature from 110°-150° C. The conjugated dimethyl-hexadiene may then be readily separated by fractional distillation. It will be appreciated that any coproduced 1,1-dihalo-4-methyl-1,4-pentadiene will also be converted to the 1,3-isomer at the same time. Since it is also this isomer of the pentadiene which is useful as an insecticide intermediate, it is possible to produce the two intermediates simultaneously, the proportions of the two products being controllable by varying the reaction conditions, as will be seen from the following Examples.

EXAMPLES 1-7

General Procedure

A solution of t-butylhydroperoxide in trichloroethylene was pumped at constant rate into a vapourising flask maintained at 160° ± 10° C. The vapour produced was mixed with a measured flow of isobutene and the mixture pre-heated at 120° ± 3° C. before entering a cylindrical silica-glass reactor (3.7 cm × 15 cm) maintained at 510° ± 10° C. Liquid products were condensed in an ice-cooled trap and analysed by gas-liquid chromatography (glc) using a 2 m 30% $\beta\beta'$ oxydipropionitrile column at 70° C. with a nitrogen pressure of 10 psig. The residence time in the tubular reactor was 20 seconds. The results are set out in Table 1, below.

Table 1

| Ex. No. | Feed Rate m mole/min | | | Ratio A:B | Yield of D calc'd on C (%) | Ratio of D:E in Product |
|---|---|---|---|---|---|---|
| | A | B | C | | | |
| 1 | 3.0 | 3.2 | 0.08 | 1:1.1 | 34 | 1:5 |

Table 1-continued

| Ex. No. | Feed Rate m mole/min A | B | C | Ratio A:B | Yield of D on C (%) | Ratio of D:E in Product |
|---|---|---|---|---|---|---|
| 2 | 3.0 | 3.2 | 0.02 | 1:1.1 | 47 | 1:12 |
| 3 | 4.0 | 2.4 | 0.02 | 1.7:1 | 64 | 1:10 |
| 4 | 4.0 | 2.4 | 0.06 | 1.7:1 | 53 | 1:6 |
| 5 | 1.5 | 5.0 | 0.04 | 1:3.3 | 25 | 1:8 |
| 6 | 3.1 | 1.0 | 0.07[(a)] | 3:1 | 51 | 1:3 |
| 7 | 3.1 | 0.63 | 0.03[(b)] | 5:1 | 67 | 1:4 |

Notes:
A = isobutene
B = trichloroethylene
C = t-butylhydroperoxide
D = 2,5-dimethyl-1,5-hexadiene
E = 1,1-dichloro-4-methylpentadiene
[(a)] di-t-butylperoxide, residence time 30 seconds
[(b)] hydrogen peroxide, residence time 11 seconds

EXAMPLES 8-10

The general procedure of Examples 1-7 was followed but the temperature of reaction was 450° C. and di-t-butyl peroxide was used as free-radical generator in a concentration of between 0.8 and 1.4 mole % of the total feed, the residence time being 10 seconds. The results are shown in Table 2.

Table 2

| Ex. No. | Total Feed (m mole) A | B | $C^1$ | Amount of D in effluent m mole | Yield of D calc'd on $C^1$ (%) | Ratio D:E |
|---|---|---|---|---|---|---|
| 8 | 36 | 24 | 0.51 | 0.32 | 63 | 2:1 |
| 9 | 48 | 12 | 0.52 | 0.21 | 40 | 3:1 |
| 10 | 54 | 5 | 0.46 | 0.14 | 30 | 10:1 |
| — | — | 60 | Nil | 0.86 | 0.04 | 4.6 | — |

Notes:
A, B, D, E as before
C = di-t-butylperoxide.

EXAMPLES 11-14

The general procedure of Examples 8-10 was followed but the ratio of A:B was maintained at 1:1 and the concentration of C' was varied as shown. The results are shown in Table 3.

Table 3

| Ex. No. | Total Feed (m mole) A | B | $C^1$ | Amount of D in Effluent m mole | Yield of D Calc'd on $C^1$ (%) | Ratio D:E |
|---|---|---|---|---|---|---|
| 11 | 30 | 29.3 | 0.135 | 0.12 | 80.5 | 1:1.8 |
| 12 | 30 | 28.5 | 0.26 | 0.21 | 80.0 | 1:1.3 |
| 13 | 30 | 28.5 | 0.52 | 0.35 | 67.0 | 1:1 |
| 14 | 30 | 26.8 | 0.99 | 0.60 | 61.0 | 1:0.6 |
| — | — | 30 | 28.5 | NII | 0.002 | — | 1:25 |

EXAMPLES 15-17

The general procedure of Examples 1-7 was followed, using an isobutene/trichloroethylene ratio of 1:1, residence time of 20 seconds and t-butyl hydroperoxide concentration of 0.2 mole % of total feed. The reactor temperature was varied from 280°-416° C. The results are shown in Table 4.

Table 4

| Ex. No. | Temp (° C) | Yield of D on C (%) | Ratio of D:E |
|---|---|---|---|
| 15 | 280 | 76 | 1:0.6 |
| 16 | 360 | 64 | 1:1.6 |
| 17 | 416 | 60 | 1:2.3 |

EXAMPLES 18-20

The procedure of Examples 15-17 was used but the ratio of isobutene/trichloroethylene was altered to 1.5 to 1 and the peroxide used was di-t-butylperoxide at a concentration of 0.13 mole %. Results are shown in Table 5.

Table 5

| Ex. No. | Temp (° C) | Yield of D on C (%) | Ratio of D:E |
|---|---|---|---|
| 18 | 430 | 83 | 1:1.45 |
| 19 | 377 | 61 | 1:0.45 |
| 20 | 200 | 40 | 1:0.31 |

EXAMPLE 21

Isolation of Products

A portion of the effluent from Example 6 was taken, containing 800 m mole trichloroethylene, 35 m mole 2,5-dimethylhexa-1,5-diene and 91 m mole 1,1-dichloro-4-methylpenta-1,4-diene. This mixture was subjected to fractional distillation, and about 600 m mole of trichloroethylene were removed slowly at > 87° C. The residue was treated with p-toluene sulphonic acid (1% by weight) in an autoclave at 150° for 4 hours under autogeneous pressure. Essentially complete isomerisation of the dienes to their conjugated isomers was effected by this treatment. The mixture was fractionally distilled to yield 2,5-dimethylhexa-2,4-diene (28 m mole) and 1,1-dichloro-4-methylpenta-1,3-diene (80 m mole).

What we claim is:

1. A process for the production of 2,5-dimethyl-2,4-hexadiene which comprises (1) dehydrodimerizing isobutene by heating it at a temperature in the range of 200°-600° C. and in the vapour phase in the presence of a peroxide which is a free-radical generator and a 1,1,2-trihaloethylene to produce 2,5-dimethyl-1,5-hexadiene; (2) isomerizing the 2,5-dimethyl-1,5-hexadiene to the conjugated 2,5-dimethyl-2,4-hexadiene prior to isolation of the 2,5-dimethyl-1,5-hexadiene, by heating the latter at a temperature in the range 100° to 170° C. in the presence of p-toluene sulphonic acid and (3) subsequently isolating the said conjugated isomer.

2. A process as claimed in claim 1 in which the peroxide is t-butyl hydroperoxide, di-t-butyl peroxide or hydrogen peroxide.

3. A process as claimed in claim 1 in which the free-radical generator is present in a concentration in the range 0.05 to 5 mole % calculated on total feed gas.

4. A process as claimed in claim 1 in which the molar ratio of isobutene to trihaloethylene is in the range 10/1 to 1/10.

5. A process as claimed in claim 4 in which the molar ratio of isobutene to trihaloethylene is in the range 1/3 to 3/1.

* * * * *